United States Patent [19]

Chien et al.

[11] Patent Number: 5,362,308
[45] Date of Patent: Nov. 8, 1994

[54] DISPOSABLE DOSAGE UNIT FOR IONTOPHORESIS-FACILITATED TRANSDERMAL DELIVERY, RELATED DEVICES AND PROCESSES

[75] Inventors: Yie W. Chien, North Brunswick; Li-Lan H. Chen, Edison, both of N.J.

[73] Assignee: Rutgers, The State University of New Jersey, New Brunswick, N.J.

[21] Appl. No.: 132,133

[22] Filed: Oct. 5, 1993

Related U.S. Application Data

[63] Continuation-in-part of Ser. No. 587,406, Sep. 25, 1990, Pat. No. 5,250,022.

[51] Int. Cl.5 ............................................. A61N 1/30
[52] U.S. Cl. ................................... 604/20; 407/152
[58] Field of Search ................ 604/20; 607/149–152

[56] References Cited

U.S. PATENT DOCUMENTS

| | | | |
|---|---|---|---|
| 4,383,529 | 5/1983 | Webster | 604/20 |
| 4,702,732 | 10/1987 | Powers et al. | 604/20 |
| 4,722,726 | 2/1988 | Sanderson et al. | 604/20 |
| 4,731,049 | 3/1988 | Parsi | 604/20 |
| 4,786,277 | 11/1988 | Powers et al. | 604/20 |
| 4,915,685 | 4/1990 | Petelenz et al. | 604/20 |
| 4,927,408 | 5/1990 | Haak et al. | 604/20 |
| 5,042,975 | 8/1991 | Chien et al. | 604/20 |
| 5,080,646 | 1/1992 | Theeuwes et al. | 604/20 |
| 5,084,008 | 1/1992 | Phipps | 604/20 |
| 5,135,480 | 8/1992 | Bannon et al. | 604/20 |

*Primary Examiner*—John D. Yasko
*Assistant Examiner*—Michael Rafa
*Attorney, Agent, or Firm*—Leroy G. Sinn

[57] ABSTRACT

Provided are disposable dosage units for use in iontophoresis-facilitated transdermal delivery which have hydrophilic polymer first and second layers, the first layer having ionic resin particles dispersed therein and the second layer having an ionized pharmaceutical contained. The second layer having on its surface a thin fabric layer bearing an adhesive layer. The polymer first and second layers are separated by a permselective membrane. Also provided are related devices and processes using the novel disposable dosage units.

11 Claims, 9 Drawing Sheets

DISPOSABLE DOSAGE UNIT FOR IONTOPHORESIS-FACILITATED TRANSDERMAL DELIVERY, RELATED DEVICES AND PROCESSES

CROSS-REFERENCE TO RELATED APPLICATION

This application is a continuation-in-part of U.S. application Ser. No. 07/587,406 filed Sep. 25, 1990 U.S. Pat. No. 5,250,022.

TECHNICAL FIELD

This invention relates to disposable dosage units for iontophoresis-facilitated transdermal delivery, iontotherapeutic devices using the dosage units in reservoir electrodes of the devices, and the reservoir electrodes.

It also provides an iontotherapeutic process for transdermal administration of ionizable pharmaceuticals, particularly those which are otherwise transdermally absorbed to a small degree or not at all. The dosage unit is adapted to be assembled as a part of either the anode or the cathode, depending upon whether the ionized pharmaceutical is cationic or anionic, so that the ionized pharmaceutical will be delivered transdermally and then be absorbed systemically when the iontotherapeutic device is in operation.

BACKGROUND ART

Many pharmaceuticals are required to be administered by injection. Other pharmaceuticals may be administered orally, but in some cases, there is inefficient absorption into the bloodstream to permit the pharmaceuticals to achieve the intended therapy. Also, with regard to oral administration, many orally administered pharmaceuticals undergo a high degree of destruction by the hepato-gastrointestinal first-pass metabolism. Often the metabolites of the first-pass metabolism cause unwanted biological activity or toxicity. In oral administration, there are variables which cause undesirable variations in the extent of gastrointestinal absorption from subject to subject, especially in the case of some pharmaceuticals; and there are also associated problems of uneven blood levels resulting from an initial large absorption with attendant undesirable side effects or toxicities, and subsequent blood levels which are less than therapeutically optimal.

There has been an increasing interest in transdermal delivery. However, transdermal absorption of a number of pharmaceuticals has not been satisfactorily developed for adequate therapy, since they have not been absorbed transdermally to any significant degree.

Investigations have been carried out to explore the delivery of certain therapeutic agents transdermally by use of iontotherapy. Development of previous reservoir electrode devices have been reported, for example, by Sanderson et al., U.S. Pat. No. 4,722,726 and references cited therein.

It is highly desired to provide new and improved iontotherapeutic devices, reservoir electrodes therefore, and iontotherapeutic processes and disposable dosage unit forms for use with the reservoir electrodes and to provide further thereby therapeutic levels of systemically-active pharmaceuticals efficiently with a physiologically-acceptable low electric current.

SUMMARY OF THE INVENTION

Provided by this invention is a pharmaceutical dosage unit adapted to be removably assembled with a reservoir electrode of a transdermal periodic iontotherapeutic system, said dosage unit to be used in electrical contact with intact skin to be iontotherapeutically treated to administer transdermally a systemically effective dose amount of an effective and transdermally absorbable amount of an ionized pharmaceutical; said dosage unit comprising solution of said ionized pharmaceutical dispersed therein having an iontotherapeutically effective and physiologically acceptable pH at least about one pH unit lower or higher than the pKa or isoelectric point of said pharmaceutical; said unit dose adapted to permit said pharmaceutical to be released upon application to the reservoir electrode of an effective pulsed DC current; said dosage unit having the following elements:

a. a dimensionally stable hydrophilic gel polymer first layer which comprises a hydrophilic polymer which has dispersed therein an ionic exchange resin which is effective in removing the ions generated by the electrode during the operation of the iontotherapeutic system;

b. a permselective membrane which is intimately adhered to the top surface of the hydrophilic polymer first layer which has a pore size sufficiently small to prevent any substantial passage of the pharmaceutical through the membrane;

c. a hydrophilic gel polymer second layer intimately adhered to the top surface of the permselective membrane and having dispersed therein an effective dose amount of an ionized pharmaceutical solution, said solution having a pH at least one pH unit below or above the pKa or isoelectric point of the pharmaceutical;

d. a thin fabric disc intimately adhered to the hydrophilic gel polymer second layer; and e. an adhesive polymer third layer being in intimate contact with the thin fabric disc and providing intimate contact with the skin of a subject being treated;

said dosage unit adapted to be received by the pharmaceutical reservoir electrode and to make electrical contact with the electrical terminus of said pharmaceutical reservoir electrode.

Desirably, a thin fabric disc will also be applied in intimate contact with the surface of the hydrophilic gel polymer first layer before application of any protective peelable release liner film. The dosage unit can have films or release liners covering both the lower exposed surface of the hydrophilic gel polymer first layer and the adhesive polymer third layer which will be removed before assemby of the dosage unit and the reservoir electrode. In making the dosage unit wherein a suitable hydrophilic polymer is utilized, a selection is made of the hydrophilic polymer which is compatible with the ionized pharmaceutical of the dosage unit, as well as being sufficiently dimensionally stable to permit storage, transportation and utilization of the dosage unit in the iontotherapeutic device employed in administering the ionized pharmaceutical.

The hydrophilic gel polymer second layer consists of a crosslinked polymeric material which is in hydrogel form. It is desirably formed by polymerizing a solution of the suitable monomeric material catalyst and crosslinking agent therefore, the solvent being a suitable aqueous buffer. The polymerization mixture desirably can be added to a mold of the final desired shape and size. After polymerization, the layer desirably is thoroughly washed with deionized water and is dried. To the produced second layer after drying, desirably the pharmaceutical can be added to the layer by following the "swelling method", which simply is introducing the dried second layer to an aqueous solution of the ionized pharmaceutical, suitably using an aqueous buffer at the desired pH at least one pH unit below or above the pKa or the isoelectric point. The hydrophilic gel polymer second layer is permitted to take up the pharmaceutical solution until it returns to its original size and takes up the desired amount of ionized pharmaceutical.

Polyacrylamide is a presently preferred hydrophilic polymer for use in making the dosage unit. Other suitable polymers can be used, for example, in illustration, poly-2-hydroxyethylmethacrylate (referred to as HEMA), sodium carboxymethyl cellulose, and the like.

Also, it has been found desirable to incorporate along with insulin or other peptide pharmaceutical an agent which will inhibit or prevent proteolytic degradation after the ionized pharmaceutical has been transdermally absorbed in the iontotherapeutic process. One suitable agent to inhibit such proteolytic degradation has been found to be a protease degradation inhibitor, such as aprotinin. Other peptide pharmaceuticals which are ionizable can be also used in conjunction with a suitable proteolytic degradation inhibitor, either a protease inhibitor or another effective inhibitor of proteolytic degradation, which is compatible with the dosage unit and biologically compatible with the pharmaceutical component as well as the skin and body of the subject being treated.

The ionized pharmaceutical solution present in the final second layer has a dosage amount of an ionized pharmaceutical solution (pH desirably at least about 1.0, 1.5 or about 2 pH units above or below the pKa or isoelectric pH of the ionized pharmaceutical if the pharmaceutical is peptide in nature) and is dispersed in the polymer of the layer which is characterized by being compatible with the pharmaceutical as well as the skin, hydrophilic, and capable of releasing the pharmaceutical for iontotherapeutic transdermal absorption.

Desirably, the dosage unit also comprises a housing element which assists in assembly of the dosage unit with the reservoir electrode and the disassembly when it is desired to replace the dosage unit. The housing element will have an opening at the bottom to permit electrical contact of the hydrophilic gel polymer first layer having dispersed ionic exchange resin with the terminus of the iontotherapeutic device.

The dosage units are maintained covered to retain sterility until the desired time of use. Further, the dosage units can be sealed under sterile conditions in individual pouches.

The pharmaceutical reservoir electrode which will receive a dosage unit of this invention is used as a part of a suitable iontotherapeutic device, which can be used to carry out the iontotherapeutic delivery and transdermal absorption of the ionized pharmaceutical. The pharmaceutical reservoir electrode is either a cathode or an anode depending upon whether the pharmaceutical is in anionic or cationic form, respectively. The iontotherapeutic device desirably provides, in the process, an iontotherapeutically effective and physiologically acceptable periodic pulse current with a specific waveform having an amplitude up to about 10 mA based on a reservoir electrode skin-contacting area of about 5 $cm^2$ and an effective frequency of at least about 10 Hz up to about 50 KHz until the subject treated has received a pharmacologically-effective systemic dosage of the ionized pharmaceutical.

The pharmaceutical in the dosage unit can be selected from pharmaceuticals which can be ionized, including those which ordinarily are not transdermally absorbed through intact skin in an effective dosage amount, such pharmaceuticals including but not limited to insulins, vasopressin, heparin, growth hormones, glucagon, oxytocin, calcitonin and other macromolecular drugs as well as a number of others which can be provided in ionized form. A number of compounds which are naturally-occurring in humans, and which often are peptide in nature, are also included within this pharmaceutical group, many of which can be produced identically or as a related compound using DNA recombinant or other biological techniques.

DETAILED DESCRIPTION OF THE INVENTION AND THE PREFERRED EMBODIMENTS

Figure 1:
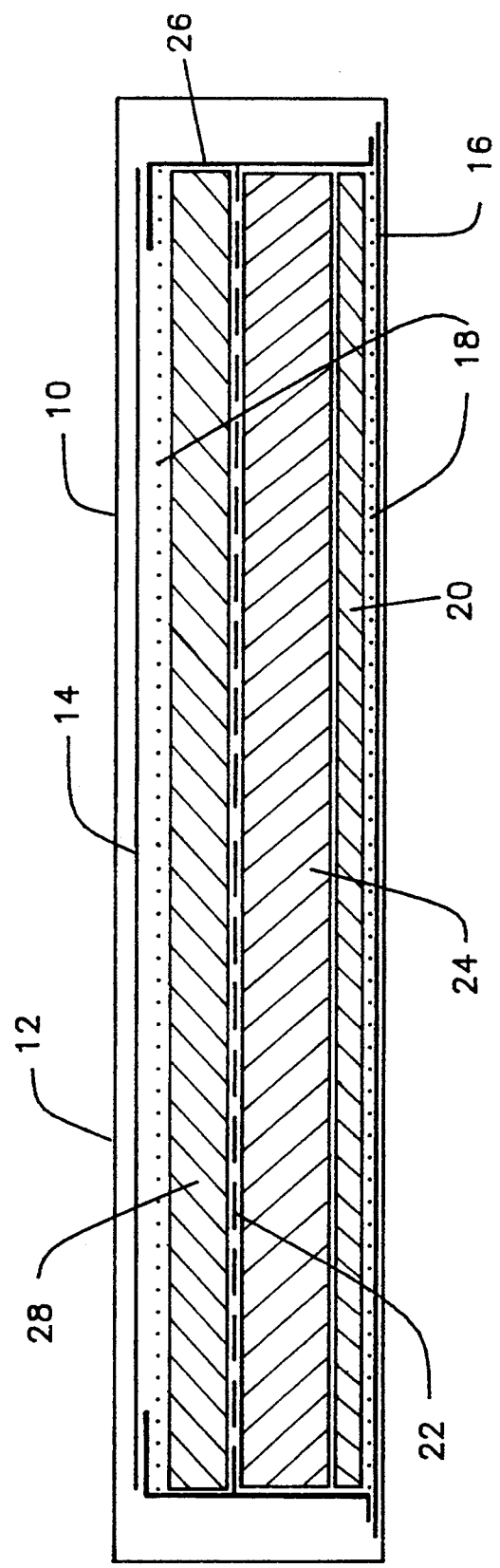
FIG. 1 is a cross section of a dosage unit of the invention having a protective holder with an opening at the bottom to permit contact with the terminus of the reservoir electrode of the iontotherapeutic device with which it is used and contained within a protective pouch.

FIG. 1 is a cross section of disposable dosage unit of the invention. The dosage unit is contained in a protective pouch 12, which can be made of a polymeric material or other suitable material. Suitable polymeric material can be selected from high density polyethylene, polypropylene, polyvinylchloride, polycarbonate, polystyrene or the like. The pouch 12 can be molded following conventional molding procedures. The pouch is shaped to receive and to protect the dosage units. The dosage unit is secured and protected by housing element 26, which also can be formed of a biocompatible polymer following conventional molding procedures, such polymers can be linear polyethylene or polypropylene, polytetrafluoroethylene or the like. In the housing element 26 is the dosage unit comprising a hydrophilic gel polymer layer 28 which has dispersed therein an effective amount of an ionic exchange resin. Adhered to layer 28 is a permselective membrane 22, which separates layer 28 from the hydrophilic gel polymer second layer 24, which contains in solution an ionized pharmaceutical having a pH at least one pH unit below or above the pKa or the isoelectric point of the pharmaceutical. The membrane 22 has pores which are preferably sufficiently small to inhibit the pharmaceutical molecules present in the second layer 28 from substantial migration into first layer 28 but are sufficiently large to permit full aqueous contact of the electrolytic solutions contained in the first and second layers. A suitable permselective membrane is selected depending upon the pharmaceutical being iontotherapeutically administered, and the pH selected for the electrolytic solutions contained in the first and second chambers. Illustrative permselective membranes are commercially available as Nucleopore membranes, Millipore membranes, Spectra/por membranes and others.

A hole is centrally disposed in the base of housing element 26 to permit passage of an electrode, which is attached electrically to the iontotherapeutic system. The electrode can be formed of any suitable electrically conductive material to make intimate electrical contact with the first polymer layer 28. The electrode can be suitably shaped from a metallic foil, e.g., from platinum foil. The first layer has dispersed therein suitable anionic or cationic resin particles. The resin particles are dispersed in the first layer 28 in a manner to inhibit an increase in the ionic content of the electrolytic solution of the first layer 28 during operation of the iontotherapeutic process wherein the electrode is an assembled element of the iontotherapeutic device used in carrying out the process. A more full description of the preparation of first polymer layer follows herein. Shown also is the second polymer layer 24, which is formed of a polymeric hydrogel. The upper surface of the polymer second layer 24 will be brought into intimate electrical contact with permselective membrane 22. The preparation of dosage unit will be described in greater detail hereinafter.

Layer 20 is an adhesive polymer layer and discs 18 are discs of thin fabric. Layer 20 is made of a hydrophilic polymer such as linear polyacrylamide. Discs 18 can be made of thin non-woven rayon.

Figures 2, 2A:
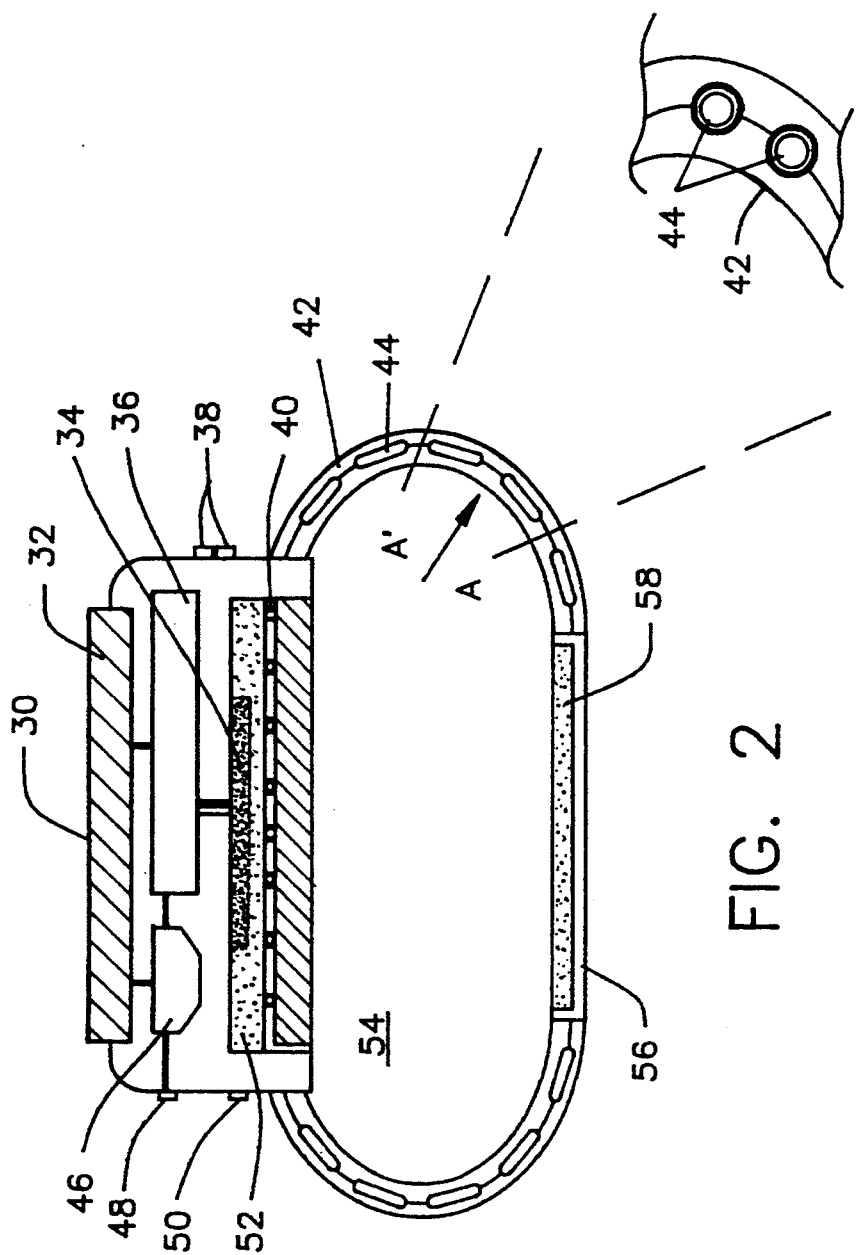
FIG. 2 is a cross section of a portable iontotherapeutic device with a wrist band which can be attached to a subject being treated iontotherapeutically, said device having integrated therein a dosage unit of the type shown in FIG. 1 and showing miniature batteries in the wrist band which power the device.
FIG. 2A is a top plan view of the A—$A^1$ segment of the batteries showing their circular shape.

FIG. 2 is a cross section of a wrist watch-type electrotherapeutic system 30 using a dosage unit of the invention 54. Ion exchange resin particles 52 are shown in the polymer first layer of the dosage unit. Permselective membrane 40 is shown separating the polymer first and second layers. The iontotherapeutic system is shown comprising liquid crystal display 32, active electrode 34, integrated circuitry 36, controllers 38, wrist band 42, miniature batteries 44, microprocessor 46, computer connection 48, sensor connection 50, receptor electrode 56 and hydrophilic gel polymer layer 58.

FIG. 2A shows segment A—A$^1$ of a top view of circular miniature battery cells connected in series as could be seen from the inner side of wrist band 42.

Figure 3:
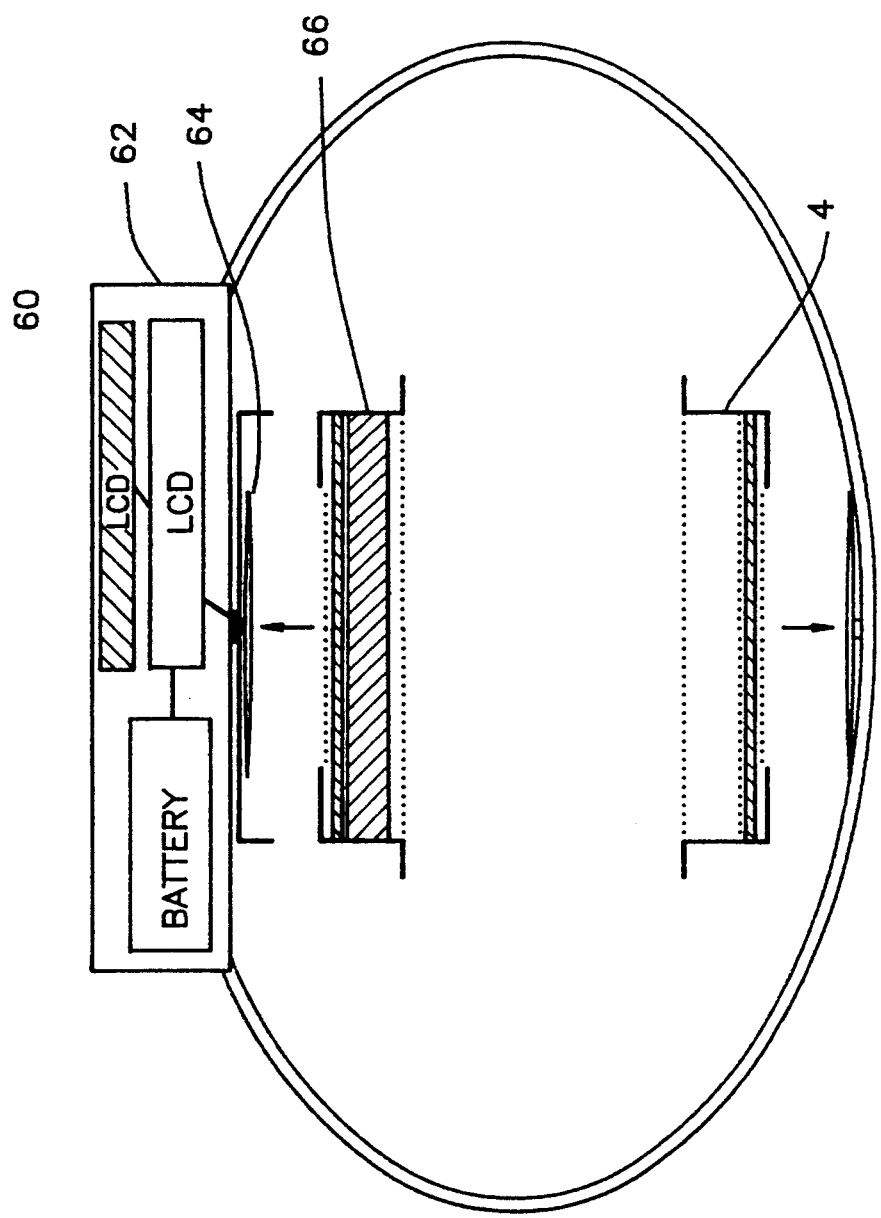
FIG. 3 is a cross section of another embodiment of a portable iontotherapeutic device of the invention showing a battery power source, liquid crystal display, integrated circuitry, a reservoir electrode with a dosage unit of the invention, a wrist band for attachment of the iontotherapeutic device to the wrist of the subject treated, said wrist band having a receptor electrode in the wrist band opposite the installed unit dose.
Figure 4:
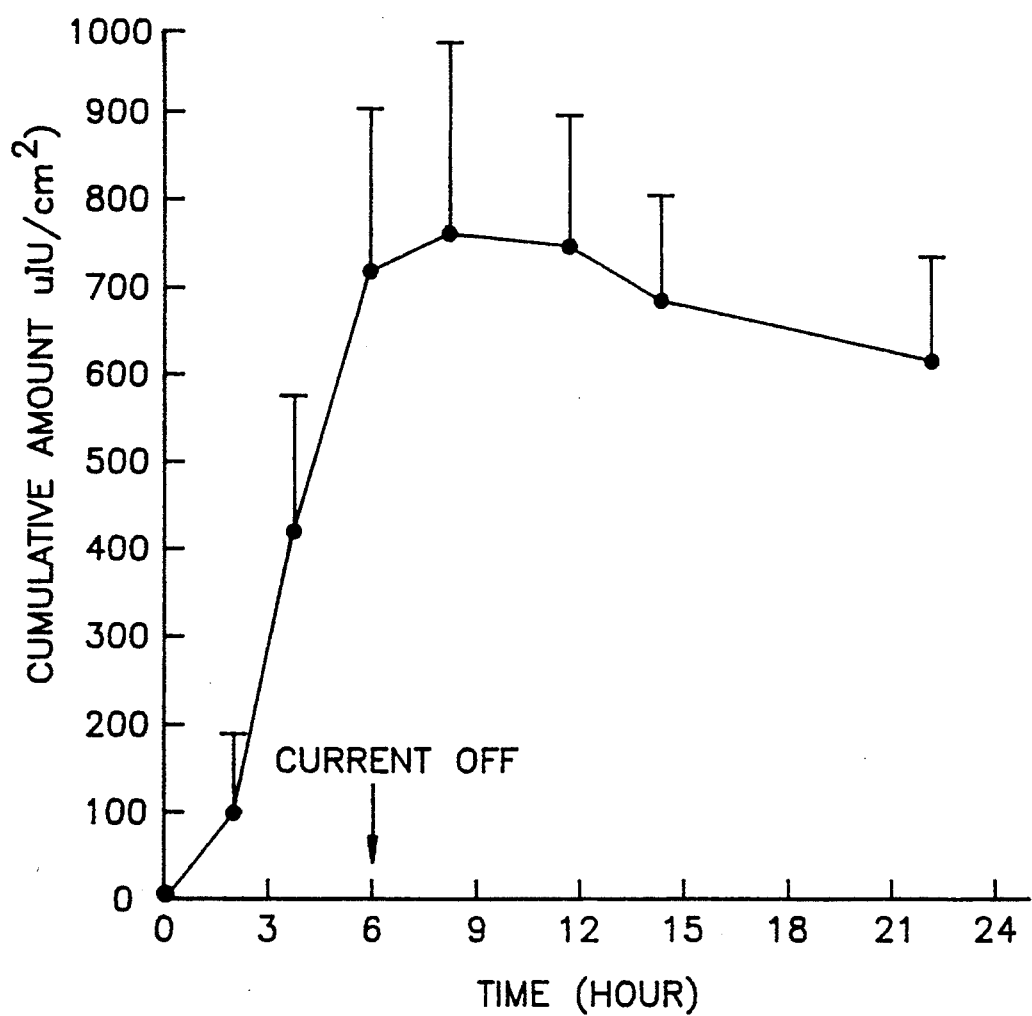
FIG. 4 is a graph showing a permeation profile of iontophoretic delivery of insulin.
Figure 5:
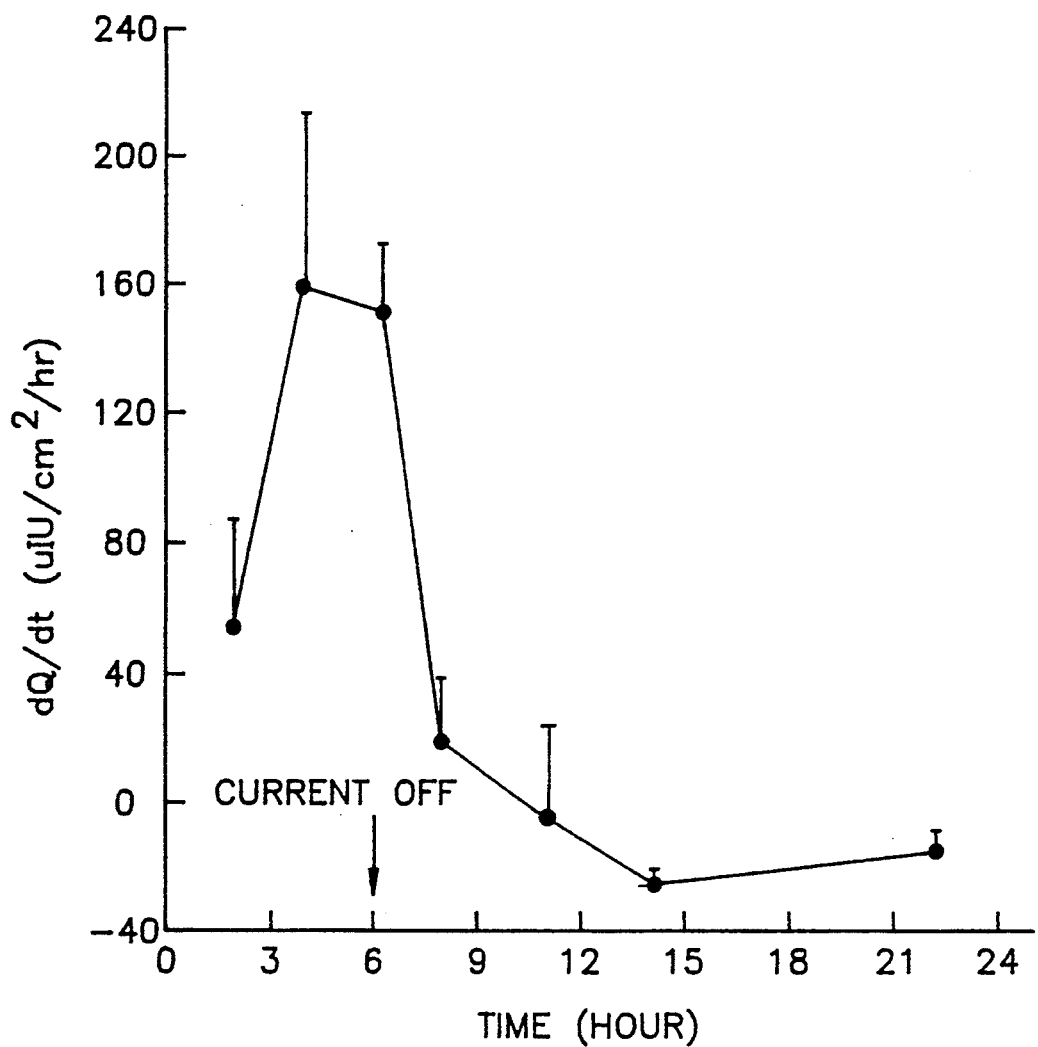
FIG. 5 is a graph of the permeation flux of iontophoretic delivery of insulin.
Figure 6:
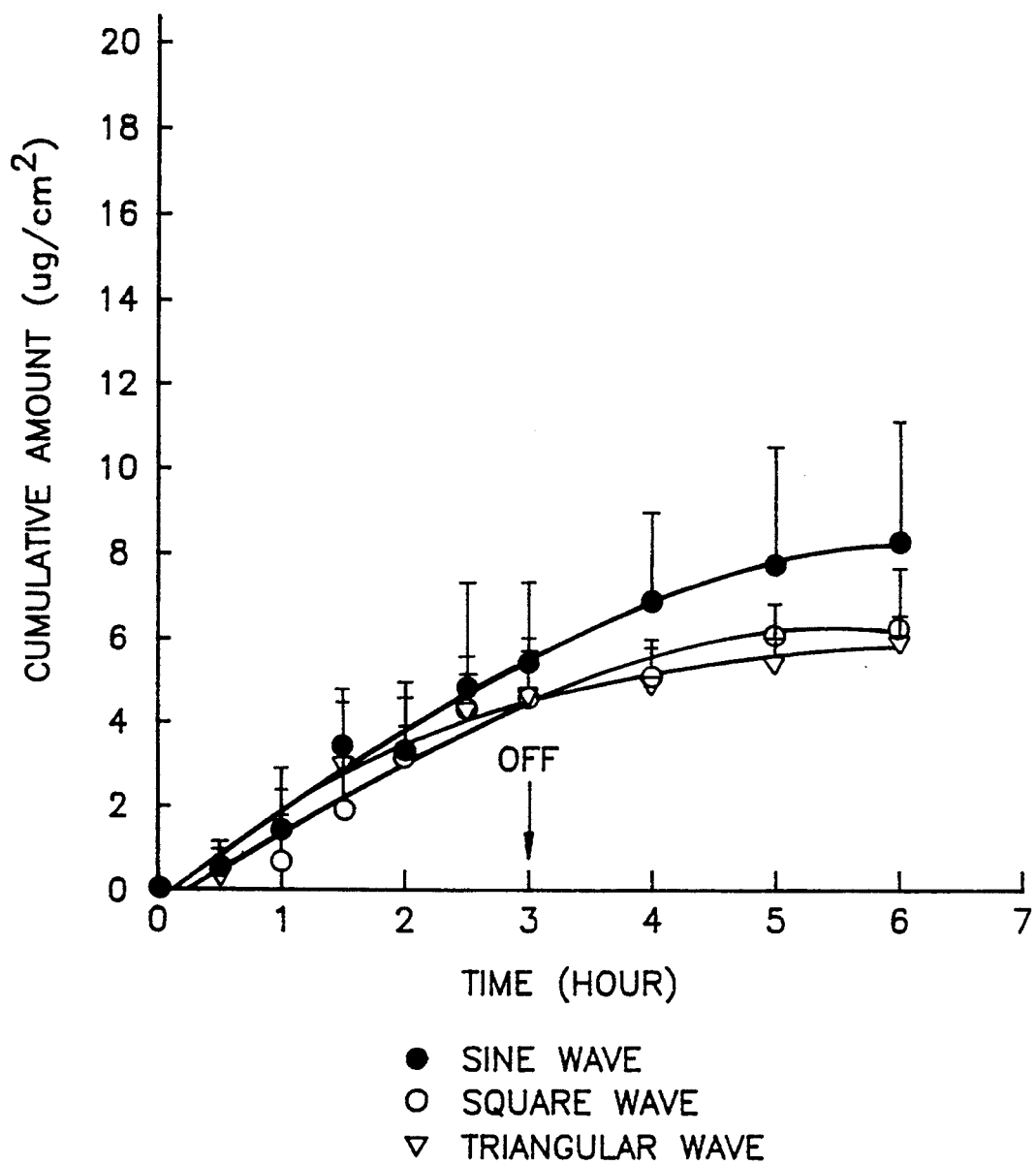
FIG. 6 is a graph showing the effect of different waveforms on the in-vitro iontophoretic permeation of luteinizing releasing hormone (LHRH).
Figure 7:
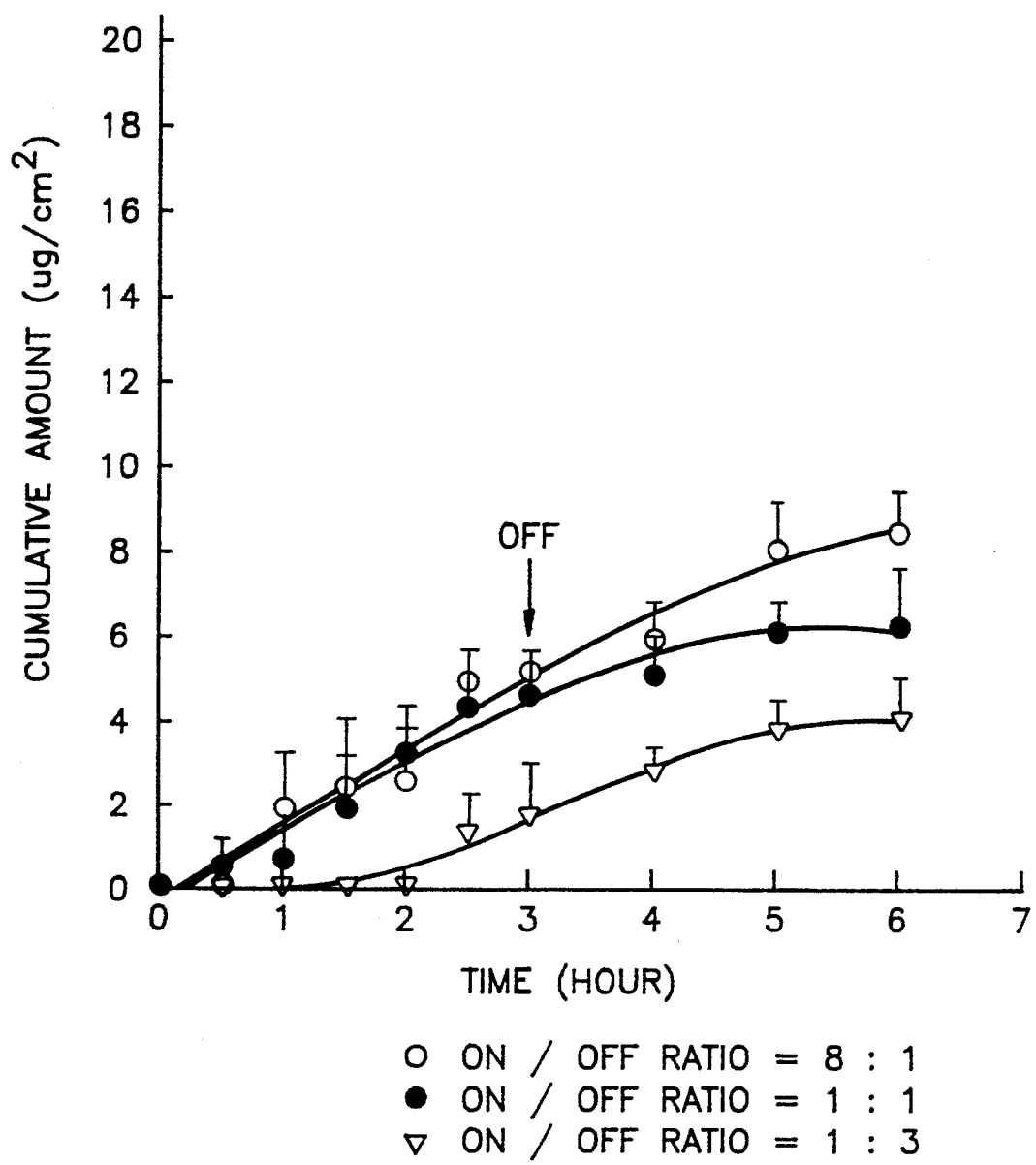
FIG. 7 is a graph showing the effect of on/off ratio of pulsed current on the in-vitro iontophoretic permeation of LHRH.
Figure 8:
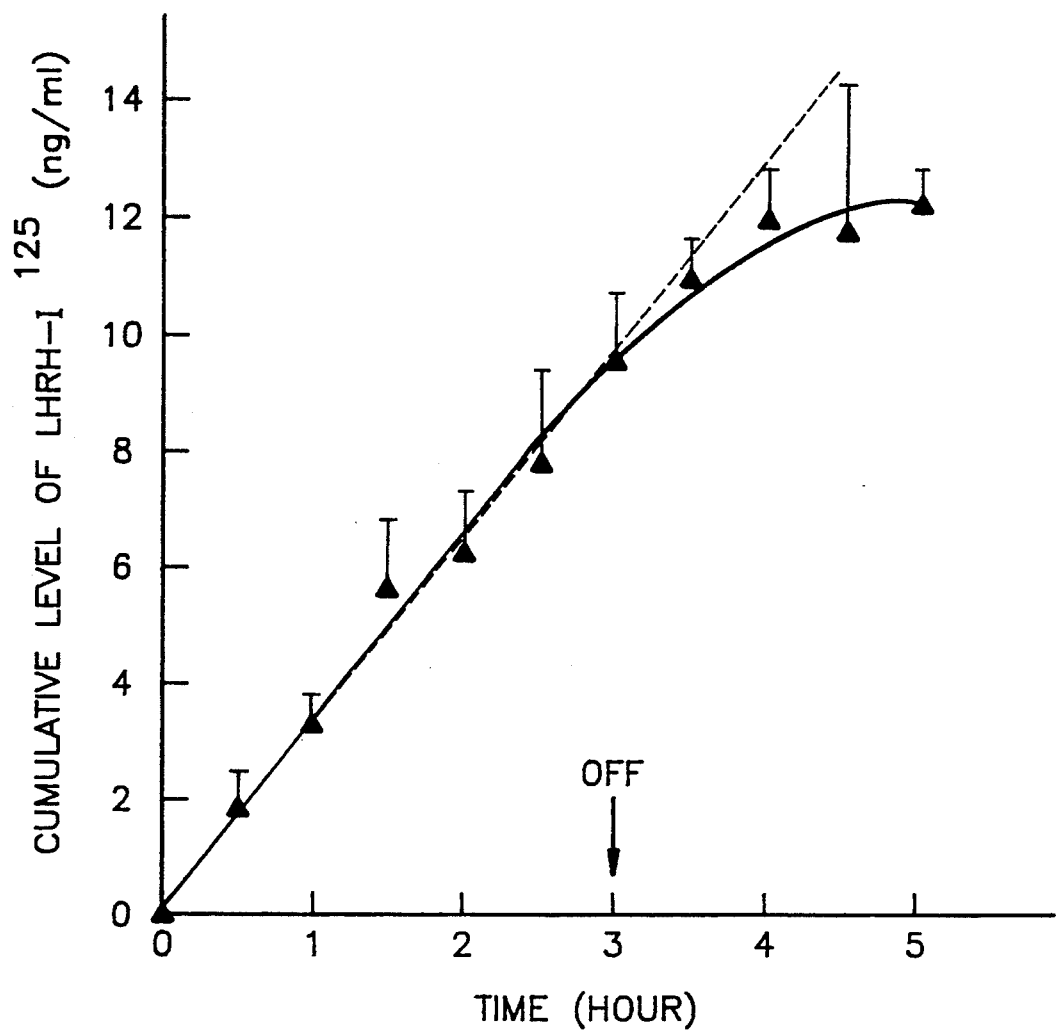
FIG. 8 is a graph showing the pharmacokinetic profile of LHRH in rats by iontophoretic delivery.
Figure 9:
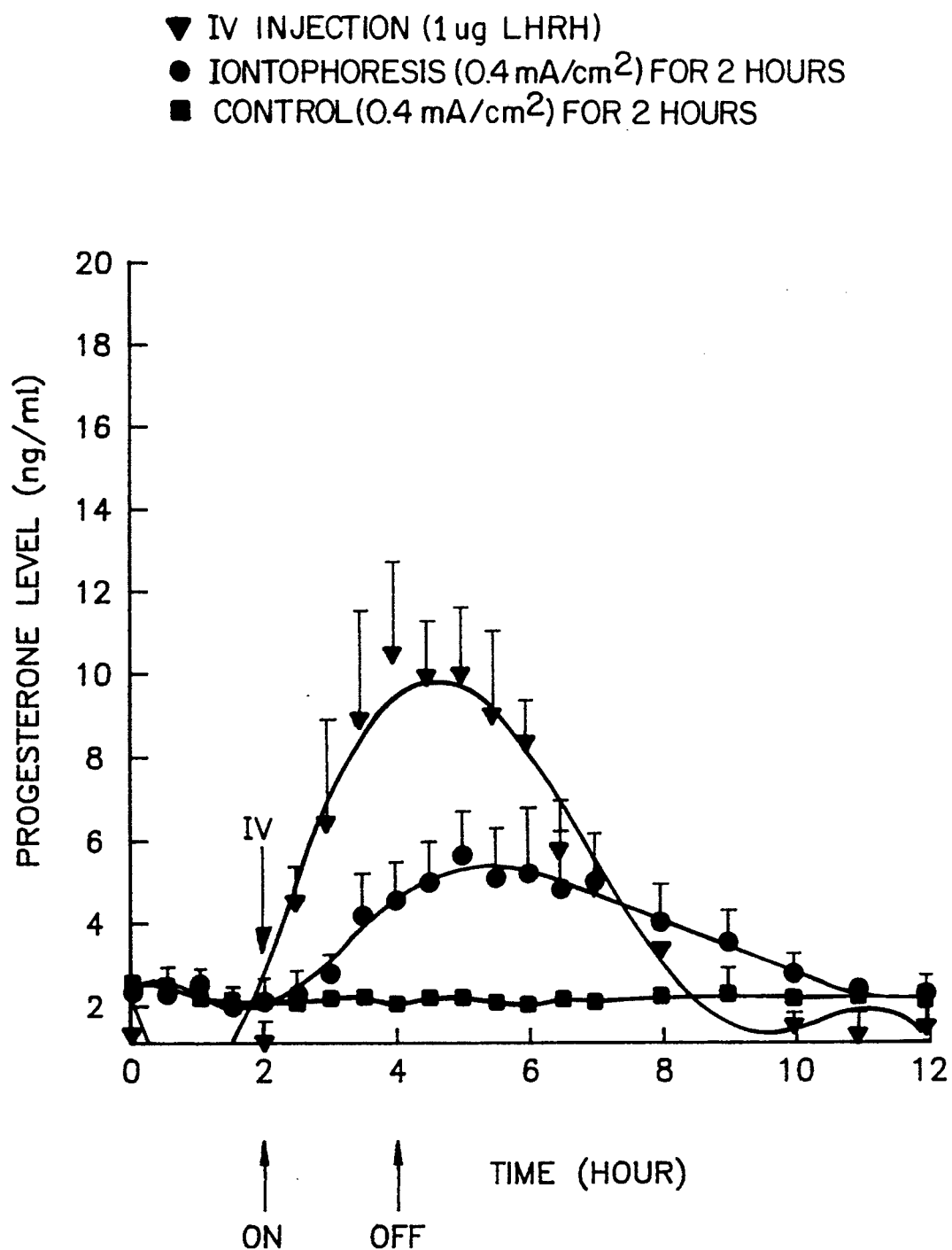
FIG. 9 is a graph showing the pharmacodynamic response of LHRH in female rabbits by iontophoretic delivery.

FIG. 3 is a cross section of another wrist watch-type electrotherapeutic system 60. It has a programmable electronic device 62, and platinum electrode 64, which is connected electrically to programmable electronic device 62. Disposable dosage unit 66 of the invention is shown as it is assembled with the reservoir electrode. Receptor electrode 68 is shown as it is assembled.

In illustration, a unit dose can be made using polyacrylamide as a hydrophilic polymer and insulin as the pharmaceutical. The pharmaceutical insulin is dissolved in a buffer solution. A suitable aqueous buffer for use is a citrate buffer having a pH at least 1 and preferably at least 2 pH units below the isoelectric pH of insulin (pH 5.3 - isoelectric point of natural commercial insulin). A suitable ionic strength is also used. A suitable buffer has been found to be a pH 3.6 citrate buffer, ionic strength 0.64 mM. It is convenient to use a buffer of higher ionic strength to permit dilution through addition of the pharmaceutical solution and other additions to enable a final desired ionic strength. Using a buffer of double the final desired strength has been found suitable.

To 100 parts by weight of the double strength buffer, 15 parts by weight of acrylamide can be added and stirred to dissolve the acrylamide, which provides a 7 percent by weight of acrylamide. To this is added a suitable crosslinking agent. For this purpose, bis-acrylamide has been used. An amount of 1.05 parts of the total volume of acrylamide buffer solution is added. To this solution, it has been found suitable to add a preservative agent. It has been found suitable to add gentamycin sulfate at about 50 micrograms/ml of the solution and 50 micrograms of bacitracin per ml of the solution. Also, it has been found desirable to add urea to the solution in a suitable amount, for example at a concentration of about 2 mg/ml solution (or other suitable agent) to minimize adsorption of the pharmaceutical to the polymer used to make the unit dose and further to inhibit the aggregation of the insulin molecules to form fibrils. The solution is stirred to form a uniform solution.

A catalyst system of ascorbic acid (0.1 percent, w/v), ferrous sulfate (0:0025 percent, w/v) and hydrogen peroxide (0.03 percent of 30 percent stock, w/v) has been found suitable to polymerize acrylamide in forming the unit dose.

The ascorbic acid and ferrous sulfate catalyst components are added to the acrylamide solution with stirring. Amounts of the acrylamide solution are added to suitable molds of the shape of the reservoir electrode. Molds made of polyethylene tetrafluoride, sold under the designation Teflon, have been found suitable for use in making dosage units and a suitable amount of the solution to form an individual dosage unit has been found to be 220 microliters. A greater or lesser amount can be used depending upon the volume of the hydrophilic gel polymer second layer and other factors. Then, a suitable polymerizing amount of hydrogen peroxide (or other suitable initiator), is added to initiate polymerization. A 10–15 microliter dilution has been found suitable. The acrylamide solution is stirred gently for a brief period. In a short time, such as about one-half minute, polymerization occurs to provide a hydrophilic gel polymer second layer consisting of a transparent hydrogel layer.

The above procedure in the alternative can be repeated using another polymer as the hydrogeled material. Again, monomeric material is employed and is polymerized. The final polymeric hydrogel material is poly-2-hydroxyethylmethacrylate (referred to as p-

HEMA). The p-HEMA polymer hydrogel can be prepared in crosslinked form by utilizing the following illustrative composition: HEMA, 40%; ethylene glycol dimethacrylate (referred to as EGDMA), 0.8%; suitable catalyst, such as the azonitrile catalyst, 2,2'-azobisisobutyl nitrile (referred to as AIBN), 0.02%; water, 35%; glycerin, 25%. All the ingredients of this composition are mixed together. AIBN and EGDMA can be added in appropriate small quantities from concentrated stock solutions dissolved in ethanol. A mixture of HEMA, a crosslinker, initiator, water and a plasticizer (glycerin) can then be purged with nitrogen for a period of time to remove oxygen, for example, 5–30 minutes.

The polymerization mixture can then be added to a suitable molds, such as polytetrafluoroethylene molds. The molds are covered suitably by use of polytetrafluoride films. Polymerization is then carried out at an elevated temperature suitable for the polymerization, such as 90° C. for an appropriate time. It has been found suitable to employ about one hour.

Upon polymerization, the final transparent polymer discs are removed from the molds and are extracted thoroughly with distilled water to remove residual polymerization mixture or components such as the monomer. It has been found that continuous extraction with deionized water for a 48-hour period is ordinarily sufficient. The polymer discs provided are dried, as by air drying at room temperature for 48 hours.

Insulin solution using pH 3.6 citric buffer can be used to add insulin to the dried polymer discs by the "swelling method". The polymer discs are placed into an insulin solution resulting in the polymer discs to take up insulin. The insulin solution used can suitably be 0.65 mM. The concentrated citric buffer is added as referred to above, i.e., 0.1 mM. Therefore, after a period of time the polymer discs take up the desired amount of insulin, the insulin discs are removed from the insulin solution and are wiped to remove residual solution remaining on the surface of the unit doses.

In summary, suitable momomeric materials can be employed along with suitable crosslinking agents to provide the crosslinked gel polymer layer containing in the final dosage unit a unit dose amount of a selected ionized pharmaceutical wherein the crosslinked polymer hydrogel is biocompatible, compatible with the ionized pharmaceutical and capable of releasing the ionized pharmaceutical to be administered in the iontotherapeutic process. Sufficient crosslinking of the hydrogel polymer should be provided to result in dimensionally stable dosage units. The final polymer disc ("the hydrophilic gel polymer second layer") should be free of unwanted polymerization composition residues such as residual monomer and catalytic components.

Also, if desired, certain pre-polymerized non-crosslinked polymers can be employed to intermix with an aqueous solution of a selected ionized pharmaceutical, which is appropriately buffered or adjusted in pH, for example, at least one or two pH units below the pKa or the isoelectric point of the pharmaceutical if the pharmaceutical is peptide in nature. The polymer and aqueous buffer solution of the ionized pharmaceutical can then be crosslinked using a suitable crosslinking agent for the polymer which has appropriate crosslinking sites such as points of unsaturation. In making the selection of such polymers and such crosslinking agents, it must be born in mind the stability of the pharmaceutical in such final dosage units after the crosslinking and the adequacy of the release factor of the pharmaceutical to assure desired iontotherapeutic absorption is achieved.

As expressed above, suitable proteolytic degradation inhibitors or combinations thereof can be added to the insulin solution or other peptide solutions used in the dose unit preparation to inhibit proteolytic degradation upon the absorption of the pharmaceutical into the skin. For example, aprotinin, a proteolytic degradation inhibitor, can be added to the insulin solution (or peptide pharmaceutical solution) used in the unit dose preparation. It has been found that about 0.1 to about 0.2 mM concentration of the proteolytic degradation inhibitor is suitable, desirably a 0.15 mM concentration is used. It is desirable to employ a pH in the dose unit substantially below or above the isoelectric pH of the proteolytic degradation inhibitor employed.

Preparation of other hydrophilic gel polymer second layers can be carried out by selecting other ionizable pharmaceuticals including other peptide pharmaceuticals such as vasopressin, growth hormone, calcitonin and the like.

In carrying out the iontotherapeutic process using the dosage units and the reservoir electrode devices provided herein, an iontotherapeutic device for the administration is employed. An iontotherapeutic device as illustrated in FIG. 3 can be employed in this administration.

In carrying out the iontotherapeutic process of this invention, a dosage unit as provided herein is utilized with a reservoir electrode as provided herein. The electrode therapeutic device utilized can be as illustrated by FIGS. 2 and 3. In FIG. 3, the power source 96 can be a suitable button type battery, such as a 6-volt battery. The integrated circuitry utilized can be selected from known circuits for iontotherapeutic devices. It is desirable to utilize circuits as shown in International Patent Publication WO-88/00846, published Feb. 11, 1988, which is incorporated herein by reference. It is preferred to utilize integrated circuitry which provides periodic DC current in the iontotherapeutic administration. It is preferred to utilize pulse current in the administration of up to about 10 mA based on a reservoir electrode/skin-contacting area of about 5 $cm^2$. Current density is suitably in the range of about 0.1 to about 1 $mA/cm^2$, desirably about 0.5 to about 0.8 $mA/cm^2$, with about 0.6 $mA/cm^2$ having been found satisfactory. In the administration, it is preferred to use a periodic waveform in the square, triangular, sinusoidal, trapezoidal, or other acceptable geometric forms, or combinations thereof.

Further, the circuitry desirably provides an on/off ratio of from 1/50 to 10/1. Additionally, it is desired to utilize a physiologically acceptable repetition frequency of at least about 10 Hz up to about 50 KHz, or more if physiologically acceptable.

Some pharmaceuticals, especially certain relatively low molecular weight pharmaceuticals, can be iontotherapeutically administered using periodic DC mode or periodic wave mode. For example, the periodic DC mode can be "on" for about 0.5 to about 60 minutes, preferably about 1 to about 30 minutes per hour. During the intervening period during the hour, the device is in "off" position. The "on" can be more frequent or less frequent as desired to provide effective treatment. In the dosage currents, the on/off ratios in the dosage units and the devices described herein can be used or adapted to be used in the practice of the iontotherapeutic process of this invention.

A few hours duration of treatment each day following either procedure is ordinarily adequate, for example, two to ten hours, depending upon factors such as the pharmaceutical, the subject being treated, the iontotherapeutic factors selected and the like.

With regard to the making of the hydrophilic gel polymer second layer, there are a number of polymers which also can be used. In general, the polymer must be essentially non-ionic, hydrophilic and compatible with the ionized pharmaceutical and the skin. The polymer used in making the second layer must permit the ionized pharmaceutical to be released during the operation of the iontotherapeutic device. The final polymers which are suitable in making the dosage unit are usually referred to as being in the category of hydrophilic polymers or hydrogels. These are preferably as pointed out above, selected from those that can be polymerized in situ. Also polymers which can be utilized can be selected from those which are pre-polymerized and have certain cross-linkable sites such as vinyl groups, hydroxy groups, carboxyl groups, amine groups, or other suitable groups which are suitable for crosslinking in making the unit doses of the invention. The particular polymer utilized is mixed with an aqueous solution of a pharmaceutical in which the pH of the solution is suitably adjusted to be substantially above or below the pKa or the isoelectric point if the pharmaceutical is peptide in nature.

With respect to the hydrophilic gel polymer first layers, they can suitably be in the form of a pre-formed electrolytic solution disc wherein suitable ionic exchange resin granules are suspended in the electrolytic solution having a suitable pH. The discs can be formed, generally speaking, following the procedure described above for making the hydrophilic gel polymer second layer containing the ionized pharmaceutical. A monomeric material, crosslinking agent, aqueous buffer, catalyst composition, stabilizers, preservatives and other desired ingredients can be added together with stirring. A desired amount of suitable resin granules are added and stirring or agitation is carried out adequately to get a thorough distribution of the selected ion exchange resin granules. Polymerization can be done as illustrated above with respect to the polymer second layer. The exact polymerization procedure and other procedures utilized in making this disc for utilizing as the polymer first layer can be selected in accordance with the configuration of the cavity of the first chamber. As in the case of the polymer second layer, the disc is sufficiently polymerized and crosslinked to be dimensionally stable to hold the ion exchange resin granules utilized in uniform distribution. Preferably, however, the above procedure for making the polymer second layer is followed without use of crosslinking agent or catalyst but a preformed polymer is used such as a linear polyacrylamide or other suitable polymers as described above. The composition is suitably coated onto a selected permselective membrane, as illustrated in the following Examples. The polymer mixture is dried as by air drying overnight.

The ion exchange resin granules are selected from cationic or anionic exchange resins. Cationic exchange resins have ion active groups with which cations react or are bound. The functional groups are normally acidic, for example are sulfonic, carboxylic or phenolic groups. Alternatively, the ion exchange resin can be anionic exchange resins which have ion active groups with which anions react or are bound. The anionic exchange can have in illustration a polyamine structure. Ion exchange resin used are water insoluble.

The particle size of the ion exchange resin can vary depending upon the ion exchange selected, the amount used, and other factors. It has been found that generally a particle size in the range of from 100 to about 200 micrometers, suitably about 150 micrometers. Suitable ion exchange resins of both anionic and cationic exchange types are available commercially for use in carrying out the invention.

Permselective membranes suitable for use in carrying out the invention are available commercially, as noted above. A permselective membrane will ordinarily be selected having pores with sufficiently low permeability with regard to the ionized pharmaceutical used to prevent substantial passage of the ionized pharmaceutical molecules into the polymer second layer. The permselective membranes are usually made of selected polymeric materials. The membranes will be selected which are compatible with the ionized pharmaceutical used in the iontotherapeutic administration, are stable structurally in its use in separating the polymer first and second layers and do not substantially interfere with the functioning of the desired iontotherapeutic process using the reservoir electrode having such permselective membrane.

Alternatively, the ion exchange resin granules present in the first chamber can be present in the form of a coating to a pre-formed polymeric lattice which has a shape to fit into the configuration of the first chamber. The lattice can be a series of concentric circles held in spaced relationship by cross members, can be in a form of an open celled matrix such as a honeycomb shape, or a type of ladder lattice form.

The resin granules will be selected depending upon the amount of resin that is used, the amount of ions generated during the iontotherapeutic process utilized, the pharmaceutical utilized and the length of iontotherapeutic administration and other factors. It will be apparent to those skilled in the art by the description herein what the operative amount will be in a specific iontotherapeutic process carried out according to this invention.

The hydrophilic gel polymer second layer containing the ionized pharmaceutical is laminated to the permselective membrane surface of the membrane-hydrophilic gel polymer first layer combination.

Then an adhesive layer is formed by coating a hydrophilic polymer mixture onto a release liner, such as a polyethylene liner. A suitable composition has been found to be 10 parts of glycerol, 5 parts of polyacrylamide and 85 parts of distilled water. This is applied to a suitable wet thickness to provide the desired adhesive layer. To the surface is applied a suitable thin fabric, desirably a non-woven fabric. The coated fabric is dried as by air drying overnight. The adhesive layer then is applied to the surface of the hydrophilic gel polymer second layer containing the ionized pharmaceutical. The polyethylene release liner is removed before use of the dosage unit.

Desirably, a thin fabric disc is also applied to the lower surface of the hydrophilic gel polymer first layer containing the resin particles.

The assembled dosage unit is desirably assembled with a housing element which protects the dosage unit and assists in assembly and disassembly with the reservoir electrode, as illustrated in FIGS. 1 and 3.

Additionally, it is desirable to cover the lower surface of the dosage unit with a suitable release liner until it is desired to use the dosage unit.

Finally, it is desirable to envelop the dosage unit in a suitable pouch or package for storage and shipment, such as illustrated in FIG. 1. The pouch can be a conventional bubble package.

With respect to the receptor electrode, there will be provided polymer hydrogel discs or other suitable element so as to adapt to the particular iontotherapeutic device utilized. Likewise, the shape will be such that it is adapted for use with the particular receptor electrode utilized by the iontotherapeutic device used. In illustration, FIGS. 2 and 3 show the receptor electrode to be in the form of a layer adapted to be assembled to provide the receptor electrode.

From the disclosure hereof, certain modifications will be apparent to those skilled in the art. To the extent that such modifications are within the intent of this invention, they are considered to be a part of this invention.

The following examples are illustrative of the invention but are not intended to be limiting.

EXAMPLE 1

Adhesive layer is provided as follows:

A polyethylene release liner is coated with hydrophilic adhesive polymer mixture consisting of a combination of 10 parts of glycerol, 5 parts of polyacrylamide and 85 parts of distilled water to a wet thickness of 500 μm. A non-woven fabric (100% rayon, 0.015 mm thickness) is applied to the adhesive polymer surface. The coated fabric is dried in air overnight. The coated fabric is cut in a circular shape having a diameter of 10 mm.

The hydrophilic gel polymer layer is provided as follows:

A pH citrate buffer having an ionic strength of 0.64 mM is prepared using the following formula:

| | |
|---|---|
| Citric acid. $H_2O$ | 0.0835 g |
| Disodium hydrogen phosphate 12 $H_2O$ | 0.0735 g |
| Water, qs to make | 1000 ml |

The buffer is prepared as a stock in double strength, so that allowance remains for the addition of monomers, peptides, and other additives before the volume is made up to the final desired concentration. To this buffer solution, 15% acrylamide (by weight) is added and dissolved. This is followed by the addition of bis-acrylamide (crosslinker) to the acrylamide solution in a concentration of 7% based on monomer weight (1.05% by weight of the total volume of the final solution). The catalyst system for polymerizing the monomer (acrylamide) is also added to this solution, delaying the initiator for the final step. The composition of the catalyst system is as follows:

| | |
|---|---|
| Ascorbic acid | 0.1% (w/v) |
| Ferrous sulfate | 0.0025% (w/v) |
| Hydrogen peroxide | 0.03% of 30% stock (w/v) |

This solution is then pipetted (220 microliters) into polyethylene tetrafluoride cylindrical molds (having a circular cross section of 10 mm and then it is polymerized in situ by the addition of hydrogen peroxide at a suitable dilution such as to have the requisite concentration in 10–15 microliters of dilution. The initiator is added with gentle and brief stirring. Polymerization occurs within about half a minute and very uniform, transparent hydrogen unit dose discs are obtained in the mold. Deionized water is used to wash the produced dose discs over a 48-hour period. Each disc is washed with 100 ml of water. After each 8-hour period, the water is replaced with a fresh 100 ml quantity of deionized water. At the end of the 48 hour period, the disc is removed from the water and is dried with air at ambient room temperature for 48 hours.

Insulin is added to the dried disc by the "swelling method". Insulin is dissolved in an amount of the above citrate buffer (1 mg insulin/ml citrate buffer). The dried disc is placed in the insulin solution for approximately 24 hours. During this time, the disc takes up about 200 g insulin and swells to return to its original size prior to drying. In International Units insulin units (IU), 1 mg insulin=26 IU of insulin.

The ionic exchange resin layer is provided as follows: The procedure for making this layer is essentially the procedure described above in the Example for making the adhesive polymer layer. To the mixture comprising, in parts by weight, 10 parts glycerol, 5 parts linear polyacrylamide (Polysciences, Inc. Cat. No. 2806), and 85 parts of deionized water, is added with stirring, 50 parts of a sulfonic cationic exchange resin particles having a particle size of about 100 micrometers (sodium form, AG50W-X8, sold by Bio-Rad).

The mixture is coated onto the permselective membrane Cel Gard 3500 sold by Hoechst-Celanese Corporation. It has a pore size of 0.075×0.25 microns. The polymerization mixture is coated to a wet thickness of 2000 μm. The provided ion exchange layer is air dried overnight.

The resulting ionic exchange resin layer having one surface covered with the permselective film is laminated to the above provided hydrophilic gel polymer layer containing insulin.

To the surface of the hydrophilic gel polymer layer is applied the adhesive layer having the coated non-woven fabric.

The assembled dosage unit is placed in a holder made of Teflon polymer shown in cross-section as 3 in FIG. F-2.

EXAMPLE 2

The procedure of Example 1 is repeated except luteinizing hormone-releasing hormone (LHRH) was used instead of insulin in the same weight amount to provide a LHRH disposable dosage unit. The $pH_{iso}$ of LHRH is 9.7 and the $pH_{iso}$ of insulin is 5.4.

EXAMPLE 3

Evaluations of dosage units made generally following the procedures of Examples 1 and 2 have been carried out as shown in FIGS. 3–9.

What is claimed is:

1. A pharmaceutical dosage unit adapted to be removably assembled with a reservoir electrode of a transdermal periodic iontotherapeutic system, said dosage unit to be used in electrical contact with intact skin to be iontotherapeutically treated to administer transdermally a systemically effective dose amount of an effective and transdermally absorbable amount of an ionized pharmaceutical; said dosage unit comprising solution of said ionized pharmaceutical dispersed therein having an iontotherapeutically effective and physiologically acceptable pH at least about one pH unit lower or higher than the pKa or isoelectric point of said pharmaceutical; said unit dose adapted to permit said pharmaceutical to be released upon application to the reservoir electrode of an effective pulsed DC current; said dosage unit having the following elements:

a. a dimensionally stable hydrophilic gel polymer first layer which comprises a hydrophilic polymer which has dispersed therein an ionic exchange resin which is effective in removing the ions generated by the electrode during the operation of the iontotherapeutic system;

b. a permselective membrane is intimately adhered to the top surface of the hydrophilic polymer layer which has a pores size sufficiently small to prevent any substantial passage of the pharmaceutical through the membrane;

c. a hydrophilic gel polymer second layer intimately adhered to the top surface of the permselective membrane and having dispersed therein an effective dose amount of an ionized pharmaceutical solution, said solution having a pH at least one pH unit below or above the pKa or isoelectric point of the pharmaceutical;

d. a thin fabric disc intimately adhered to the hydrophilic gel polymer second layer; and e. an adhesive polymer third layer being in intimate contact with the thin fabric disc and providing intimate contact with the skin of a subject being treated;

said dosage unit adapted to be received by the pharmaceutical reservoir electrode and to make electrical contact with the electrical terminus of said pharmaceutical reservoir electrode.

2. A dosage unit of claim 1 wherein the polymer used to make the polymer second layer is polyacrylamide.

3. A dosage unit of claim 1 wherein the polymer used to make the polymer first layer is polyacrylamide.

4. A dosage unit of claim 1 wherein the pharmaceutical is insulin.

5. A dosage unit of claim 1 wherein the pharmaceutical is LHRH.

6. A dosage unit of claim 1 wherein the pH is at least about 2 pH units below or above the pH of the pKa or isoelectric point of the pharmaceutical.

7. A dosage unit of claim 1 wherein the pharmaceutical is insulin and the pH is about 3.6.

8. A dosage unit of claim 1 wherein one or both of the polymer first or second layers is made using HEMA.

9. A dosage unit of claim 1 wherein the polymer first layer has a thin fabric disc laminated to its surface.

10. A dosage unit of claim 1 wherein the dosage unit has a housing element holding the dosage unit which is adapted for assembly with the reservoir electrode of the iontotherapeutic system used.

11. A protective pouch which contains a dosage unit of claim 1 and protects the dosage unit for storage and shipment.

* * * * *